United States Patent [19]

Patricelli

[11] Patent Number: 5,317,643

[45] Date of Patent: May 31, 1994

[54] AUDIO HELMET APPARATUS

[76] Inventor: Richard D. Patricelli, 500 3rd Ave., Aberdeen, Wash. 98520

[21] Appl. No.: 17,429

[22] Filed: Feb. 8, 1993

[51] Int. Cl.$^5$ .......................................... H04R 25/00
[52] U.S. Cl. .................................... 381/187; 381/188; 455/351
[58] Field of Search .............. 381/187, 183, 188, 205, 381/75; 379/430; 455/351, 89, 90, 100

[56] References Cited

U.S. PATENT DOCUMENTS

| | | | |
|---|---|---|---|
| 3,549,831 | 12/1970 | Forney | 381/75 |
| 3,786,519 | 1/1974 | Aileo | 381/187 |
| 4,357,711 | 11/1982 | Drefko et al. | 455/351 |
| 4,607,395 | 8/1986 | Sundahl | 455/351 |
| 4,729,132 | 3/1988 | Fierro | 2/414 |
| 4,833,726 | 5/1989 | Shinoda et al. | 455/351 |

Primary Examiner—Curtis Kuntz
Assistant Examiner—Huyen D. Le
Attorney, Agent, or Firm—Leon Gilden

[57] ABSTRACT

An apparatus including a radio receiver mounted interiorly of a welding helmet adjacent an upper edge thereof, with a plurality of speakers selectively securable adjacent an interior surface of the helmet. A modification of the invention includes a flexible semi-circular speaker cup mounting each audio head phone therewithin to enhance audio transmission, as well as hook members to secure excessive speaker wire relative to each head phone. The head phone wires are mounted utilizing cooperative hook and loop fastener strips to secure the head phone wires within the helmet, as required.

1 Claim, 4 Drawing Sheets

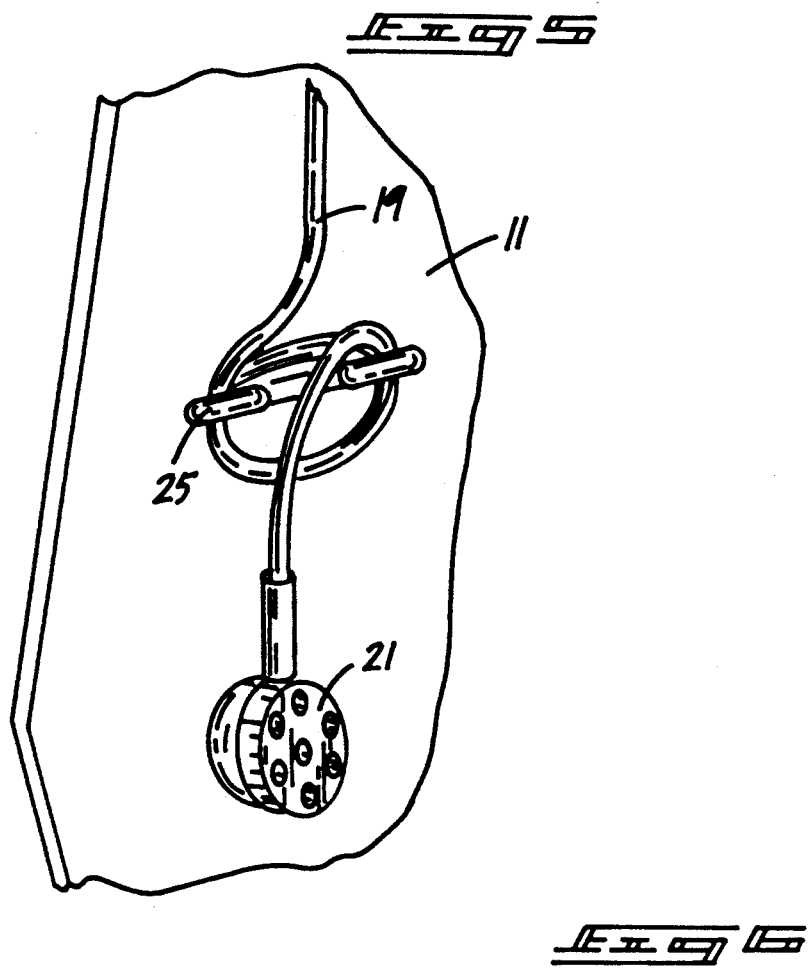
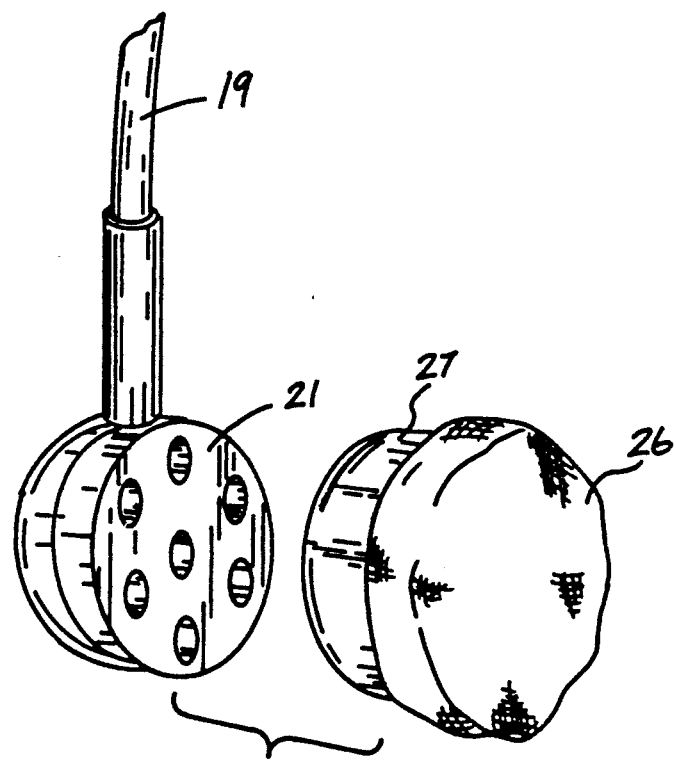

AUDIO HELMET APPARATUS

BACKGROUND OF THE INVENTION

1. Field of the Invention

The field of invention relates to welding helmets, and more particularly pertains to a new and improved audio helmet apparatus wherein the welding helmet contains a radio receiver and associated speaker arrangement mounted therewithin.

2. Description of the Prior Art

To assist in entertainment of individuals during a welding procedure, a self-contained radio receiver is provided by the instant invention to overcome boredom and monotony during repetitive or uneventful periods in a welding procedure. The instant invention attempts to overcome deficiencies of the prior art by providing such an organization with a relatively low volume output speaker arrangement to avoid distraction of an individual during a welding procedure and avoid various environmental noises to permit an individual to remain alert to various surrounding hazards. Prior art welding helmet organizations have been set forth in the prior are and have heretofore failed to provide such a self-contained unit, wherein U.S. Pat. No. 3,549,831 to Forney sets forth a welding helmet arrangement utilizing a broadcasting speaker arrangement arranged to direct a communication by an individual from interiorly of a helmet structure.

U.S. Pat. No. 3,258,534 to Goldesworthy sets forth a loud speaker arrangement in association with a safety helmet in a similar manner as the Forney organization, as noted above.

U.S. Pat. No. 4,729,132 to Fierro sets forth a sports helmet utilizing an air-activated heat generating element within the helmet structure.

U.S. Pat. No. 3,347,229 to Heitman sets forth a latch operated microphone switch for use with a breathing mask organization.

U.S. Pat. No. 3,422,224 to Curran sets forth a hat structure utilizing a microphone and an associated voice application organization.

As such, it may be appreciated that there continues to be a need for a new and improved audio helmet apparatus wherein the same addresses both the problems of ease of use as well as effectiveness in construction in providing selective entertainment to an individual to minimize boredom and mental fatigue in a welding organization, and particularly during welding for extended periods of time.

SUMMARY OF THE INVENTION

In view of the foregoing disadvantages inherent in the known types of welding helmet structures now present in the prior art, the present invention provides an audio helmet organization to permit selective directing of audio entertainment to an individual during a welding procedure. As such, the general purpose of the present invention, which will be described subsequently in greater detail, is to provide a new and improved audio helmet apparatus which has all the advantages of the prior art welding helmet constructions and none of the disadvantages.

To attain this, the present invention provides an apparatus including a radio receiver mounted interiorly of a welding helmet adjacent an upper edge thereof, with a plurality of speakers selectively securable adjacent an interior surface of the helmet. A modification of the invention includes a flexible semi-circular speaker cup mounting each audio head phone therewithin to enhance audio transmission, as well as hook members to secure excessive speaker wire relative to each head phone. The head phone wires are mounted utilizing cooperative hook and loop fastener strips to secure the head phone wires within the helmet, as required.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved audio helmet apparatus which has all the advantages of the prior art welding helmet constructions and none of the disadvantages.

It is another object of the present invention to provide a new and improved audio helmet apparatus which may be easily and efficiently manufactured and marketed.

It is a further object of the present invention to provide a new and improved audio helmet apparatus which is of a durable and reliable construction.

An even further object of the present invention is to provide a new and improved audio helmet apparatus which is susceptible of a low cost of manufacture with regard to both materials and labor, and which accordingly is then susceptible of low prices of sale to the consuming public, thereby making such audio helmet apparatus economically available to the buying public.

Still yet another object of the present invention is to provide a new and improved audio helmet apparatus which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 5 is an isometric illustration setting forth the use of a gathering hook arrangement for use in association with the speaker wire of the instant invention.

FIG. 6 is an isometric illustration of the instant invention utilizing head phone cushions.

DESCRIPTION OF THE PREFERRED EMBODIMENT

Figure 1:
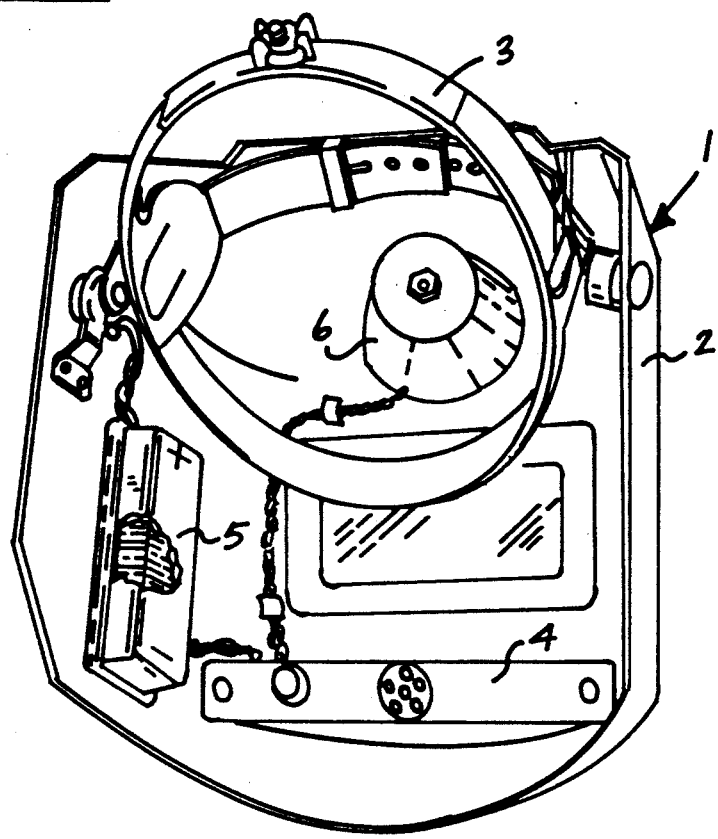
FIG. 1 is an isometric illustration of a prior art helmet construction utilizing a broadcasting microphone arrangement.
Figure 2:
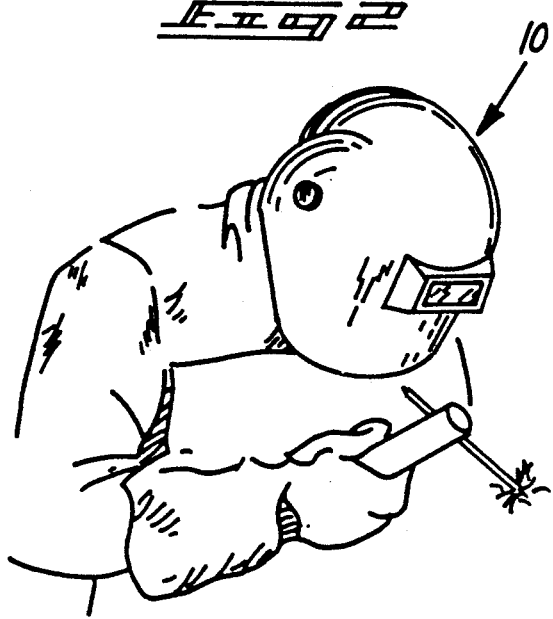
FIG. 2 is an isometric illustration of the instant invention for securement about an individual.
Figure 3:
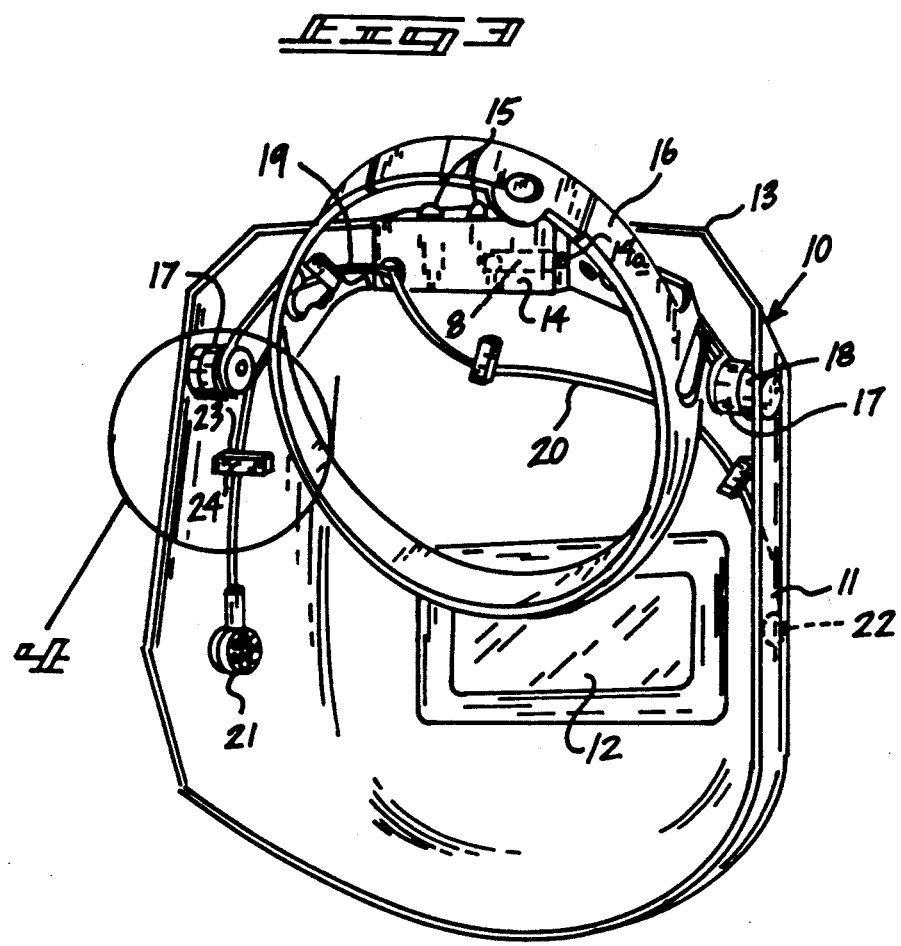
FIG. 3 is a rear isometric illustration of the instant invention.
Figure 4:
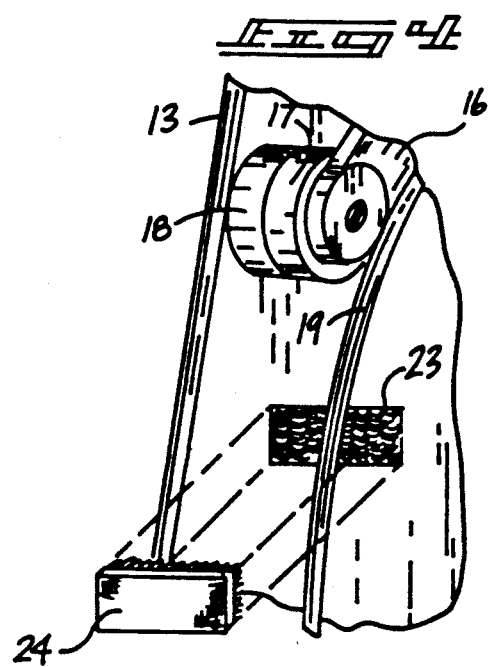
FIG. 4 is an isometric illustration of section 4 as set forth in FIG. 3.
Figure 7:
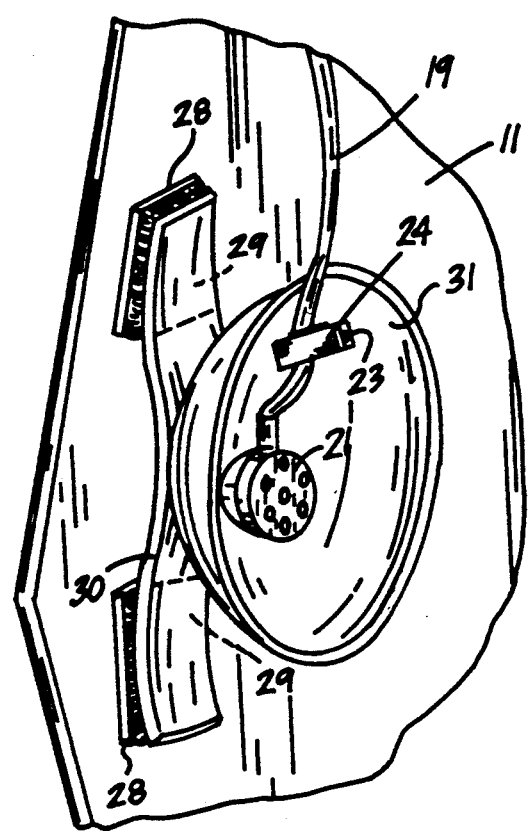
FIG. 7 is an isometric illustration of the instant invention utilizing a flexible speaker cup for use with each speaker.
Figure 8:
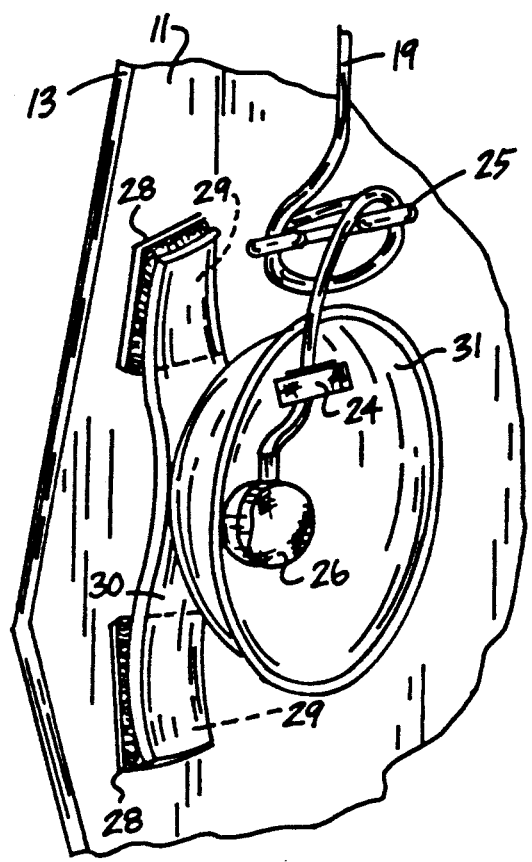
FIG. 8 is an isometric illustration of the instant invention utilizing the speaker cup as set forth in FIG. 7 in further association with the gathering hook and head phone cushion construction.

With reference now to the drawings, and in particular to FIGS. 1 to 8 thereof, a new and improved audio helmet apparatus embodying the principles and concepts of the present invention and generally designated by the reference numeral 10 will be described.

FIG. 1 illustrates a prior art helmet construction 1, wherein a helmet 2 utilizes an annular band 3 for mounting upon an individual. The helmut 2 includes an audio amplifier 4 for use with the self-contained microphone 4 to transmit an audio signal through a speaker 6 mounted above a viewing lens within the helmet construction and powered by a self-contained battery unit 5.

More specifically, the audio helmet apparatus 10 of the instant invention essentially comprises a helmet 11 defining a concave interior surface, and of a generally semi-cylindrical configuration, including a viewing window 12 mounted through a forward surface of the helmet. The helmet is of a type typically utilized in welding. The helmet 11 is formed with a continuous outer perimeter edge 13, and includes a radio receiving module 14 mounted within the interior surface of the helmet 11 adjacent to an upper edge of the perimeter edge 13. The radio module includes volume and channel selector dials 15 projecting beyond the perimeter edge 13 to provide manual access thereto, and includes a self-contained battery "B" accessible through an associated battery plate. An annular helmet band 16 is diametrically mounted to pivot mounts 17 that are in turn pivotally secured to pivot support bosses 18 that are mounted to sides of the helmet 11 adjacent side edges of the perimeter edge 13. The radio module 14 includes a first and second respective head phone transmission line 19 and 20 directed from the module and extending from the module along the interior surface of the cavity of the helmet 11, and electrically associated with a respective first and second head phone 21 and 22. The first and second head phones are disposed to opposed interior side surfaces of the helmet 11, and are mounted by use of a plurality of first hook and loop patches 23 mounted to the interior surface of the helmet and selectively securable to the interior surface of the helmet by second hook and loop fastener patches 24 formed onto a flexible web such as leather, vinyl, and other various polymerics. The radio module 14 may also be selectively mounted utilizing various fasteners, either mechanical or fabric, to secure the module to the interior surface of the helmet.

It is contemplated that the radio be of a relatively low volumetric output type to minimize distraction of an individual when utilizing the helmet, and permit the individual to be fully cognizant of an associated working environment in use.

FIG. 5 illustrates the use of a clevis hook 25 that is mounted to each side wall of the helmet 11 adjacent each side and edge of the edge 13 to adjust and gather excessive transmission line 19 or 20 relative to each respective head phone 21 and 22. FIG. 6 further notes the use of a cushion 26 formed of an audio transmissive material to avoid impairing of audio signals directed through the head phones 21 and 22, wherein each cushion 26 includes an elastomeric skirt 27 to permit securement to each respective head phone, in a manner as illustrated in FIG. 6 for example, to cushion inadvertent impact by an individual to each associated head phone in position. Further, to enhance audio radiation signals through each respective head phone, a flexible, semi-spherical speaker cup 31 is selectively mounted to each interior surface utilizing spaced third hook and loop fastener strips 28 mounted to each interior side surfaces of the helmet 11 adjacent each side edge of the perimeter edge 13, wherein an elongate strap member 30 mounts spaced fourth hook and loop fastener strips 29 spaced apart a predetermined spacing equal to a predetermined spacing between the third hook and loop fastener strips 28 to permit selective securement of the cup thereto. The flexible sphere cup 31 is mounted to provide orientation of audio signals of each head phone, and is further of a flexible material to avoid injury and absorb impact of an individual's head portion positioned within the helmet cavity of the helmet 11.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An audio welding helmet apparatus, comprising in combination,
    a welding helmet, including an elongate helmet defined by a generally semi-cylindrical configuration including a continuous perimeter edge, the perimeter edge including an upper edge portion and spaced side edge portions, and
    the helmet including a band pivotally mounted within the helmet for mounting of the helmet to an individual, and the helmet including a viewing window mounted through a forward surface of the helmet positioned medially between the side edge portions, and
    a radio receiving module mounted interiorly of the helmet adjacent the upper edge portion, and
    including a first head phone and a second head phone mounted to opposed interior side walls of the helmet in electrical communication with the radio receiving module, and
    the radio receiving module is mounted adjacent the upper edge portion of the helmet, and wherein the radio receiving module further includes respective volume and channel selector dials projecting beyond the upper edge portion to provide enhanced manual access to the dials during use of the helmet, and
    a respective first and second head phone transmission line in electrical communication with the radio receiving module, wherein the first and second head phone transmission lines are in respective communication with the first and second head phone to direct audio signals to the first and second head phones, and
    each respective first and second head phone transmission lines include a plurality of first hook and loop fastener patches fixedly mounted to the interior surface of the helmet, wherein the first hook and loop fastener patches are cooperative with second hook and loop fastener patches, and wherein each head phone transmission line is secured between the first and second hook and loop fastener patches to secure the audio transmission lines adjacent the interior surface of the helmet, and
    a clevis hook member, wherein the clevis hook member further includes a plurality of opposed hook portions to permit winding of excessive head phone transmission lines of each respective first and second head phone transmission lines thereabout to effect selective vertical adjustment of each head phone relative to each clevis hook, and
    a cushion member selectively securable overlying each head phone, wherein each cushion member includes an audio transmission cushion member, and wherein each cushion member includes an elastomeric skirt, wherein the elastomeric skirt is selectively securable about each head phone, and
    a first and second respective flexible semi-spherical speaker cup, wherein each speaker cup is mounted adjacent each side edge portion of the side edge portions of the helmet, and wherein each speaker cup is fixedly mounted to an elongate, flexible strap member, the elongate flexible strap member includes fourth hook and loop fastener portions mounted to the strap and spaced apart a predetermined distance, and the fourth hook and loop fastener portions are selectively securable to third hook and loop fastener portions spaced apart a predetermined spacing and fixedly mounted to the interior surface of the helmet adjacent each side portion thereof.

* * * * *